United States Patent [19]

Simnon

[11] Patent Number: 5,600,452
[45] Date of Patent: Feb. 4, 1997

[54] CIRCUIT FOR THE REPRODUCTION OF COLOR PRESENTATIONS OF CHRONOLOGICAL PROGRESSION

[75] Inventor: Guenther Simnon, Neunkirchen, Germany

[73] Assignee: Siemens Aktiengesellschaft, Munich, Germany

[21] Appl. No.: 340,879

[22] Filed: Nov. 15, 1994

Related U.S. Application Data

[63] Continuation of Ser. No. 76,399, Jun. 14, 1993, abandoned.

[30] Foreign Application Priority Data

Feb. 22, 1993 [DE] Germany ............................ 9302548 U

[51] Int. Cl.$^6$ ..................................................... H04N 1/46
[52] U.S. Cl. .......................................................... 358/501
[58] Field of Search .............................. 378/99, 100, 128, 378/178; 358/111, 487, 473, 474, 497, 506, 527, 500, 501, 515, 529, 537; 382/59, 6; 40/361, 363; 128/653.1, 653.2, 653.5, 903, 904; 348/31–35; 101/DIG. 29

[56] References Cited

U.S. PATENT DOCUMENTS

| | | | |
|---|---|---|---|
| 3,628,014 | 12/1971 | Grubic, Jr. | 250/49.5 A |
| 3,975,762 | 8/1976 | van den Bosch | 348/32 |
| 4,149,185 | 4/1979 | Weinger | 348/34 |
| 4,706,185 | 11/1987 | Karaki et al. | 367/110 |
| 4,758,878 | 7/1988 | Frantz | 348/32 |
| 4,851,900 | 7/1989 | Edwards et al. | 358/81 |
| 4,926,454 | 5/1990 | Haendle et al. | 378/98.5 |
| 4,992,754 | 2/1991 | Blauvelt et al. | 330/149 |
| 5,132,639 | 7/1992 | Blauvelt et al. | 330/149 |
| 5,252,930 | 10/1993 | Blauvelt | 330/149 |

FOREIGN PATENT DOCUMENTS

| | | |
|---|---|---|
| 0169273A1 | 1/1986 | European Pat. Off. . |
| 0416622A2 | 3/1991 | European Pat. Off. ........ H04B 10/18 |
| 2053894 | 5/1971 | Germany . |
| 3018129C1 | 10/1981 | Germany . |
| 3616214C2 | 12/1987 | Germany . |

OTHER PUBLICATIONS

Patent Abstracts of Japan, published Jan. 13, 1992, Hitoshi Watanabe "Semiconductor Laser Device".
16th European Conference on Optical Communication, Sep. 16–20, 1990; K. Drogemuller et al, "Frequency Modulation Characteristics of Tunable Twin–Guide (TTG) DFB Lasers".

*Primary Examiner*—Edward L. Coles, Sr.
*Assistant Examiner*—Jerome Grant, II
*Attorney, Agent, or Firm*—Hill, Steadman & Simpson

[57] ABSTRACT

A circuit arrangement for reproduction of color presentations of chronological progressions from a video signal of a video camera. The circuit arrangement comprises a switch unit for every color channel R, G, B. These switch units, operated in alternating fashion, connect the R, G, B output of the video camera to inputs of a playback unit such that the video signal is supplied to the individual color channels R, G, B at different times.

9 Claims, 2 Drawing Sheets

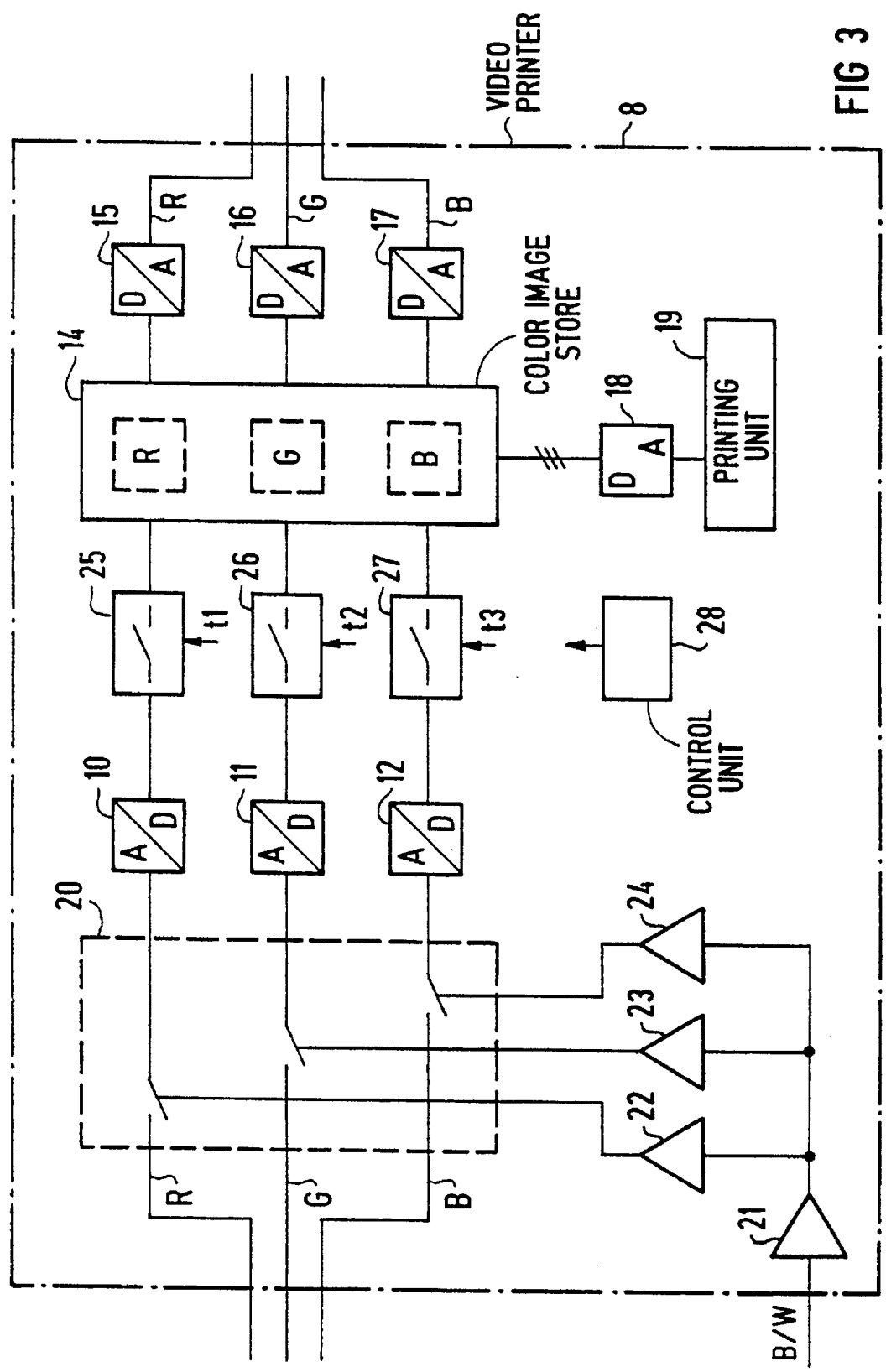

CIRCUIT FOR THE REPRODUCTION OF COLOR PRESENTATIONS OF CHRONOLOGICAL PROGRESSION

This is a continuation of Ser. No. 08/076,399 filed Jun. 14, 1993 now abandoned.

BACKGROUND OF THE INVENTION

The invention is directed to a circuit for the reproduction of color presentations of chronological progressions from the video signal of a television camera that is connected to the individual inputs of the color channels of a playback device or reproduction means such as a monitor or a hard copy device.

In hard copy devices, and what are referred to as video color printers, a color image was previously read into the image store of the video color printer, this image being isochronically present a the RGB color channels, or being present as a black/white BAS signal. The schematic diagram of such a video color printer is shown in FIG. 2. The color signals R, G, and B are present at the input of the video printer 8 and are supplied to three analog-to-digital converters (A/D converters 10 through 12). The A/D converters 10 through 12 are connected via a switch unit 13 to a color image store 14 that comprises three memories or memory areas for the three color channels R, G, and B. Three digital-to-analog converters (D/A converters 15 through 17) are connected to the color image store 14, these converters being connected to a monitor 7, a color monitor in this case, for monitoring. Furthermore, the color image store 14 is connected to the printing unit 19 of the video printer 8 via a further D/A converter 18.

Such color video printers, however, have the disadvantage that color images can only be produced from black-and-white video signals with considerable external expense because of the parallel inputs, for example with three external memories and a compensation means for transit time shifts.

SUMMARY OF THE INVENTION

It is an object of the invention to create a circuit of the type initially cited such that, in addition to enabling the normal color reproduction of color video signals, a color reproduction of chronological progressions from a black-and-white video signal (B/W) is enabled, whereby different colors are allocated to the different points in time.

According to the present invention, a circuit is provided which comprises a switch unit for every color channel, this switch unit connecting the output of the video camera to the inputs of the playback device such that the video signal is supplied to the individual color channels at different times. What is thereby achieved is that—for example in digital subtraction angiography (DSA)—the chronological path of the contrast agent from a B/W video signal can be reproduced in an image on the basis of the different colors.

According to the invention, the switch units can be operated in alternating fashion or all can be closed at the beginning of the examination and can be successively opened at specific points in time.

Given the employment of the circuit in digital subtraction and angiography, it has proven advantageous when the first switch unit is opened at the point in time of maximum arterial phase, the second switch unit is opened at the point in time of maximum intermediate phase, and the third switch unit is opened at the point in time of maximum venous phase.

According to the invention, the first color channel can thereby be red, the second color channel can be green, and the third color channel can be blue. Further, an image store can be provided for each color channel.

The circuit can also be alternatively employed for the reproduction of color signals when it comprises a respective input for the color channels and is designed such that the switch units selectively connect the inputs of the color channels to the inputs of the playback device. According to the invention, the circuit can be arranged in a video printer.

BRIEF DESCRIPTION OF THE DRAWINGS

FIG. 3 is a circuit arrangement for a video printer according to the invention.

DESCRIPTION OF THE PREFERRED EMBODIMENTS

Figure 1:
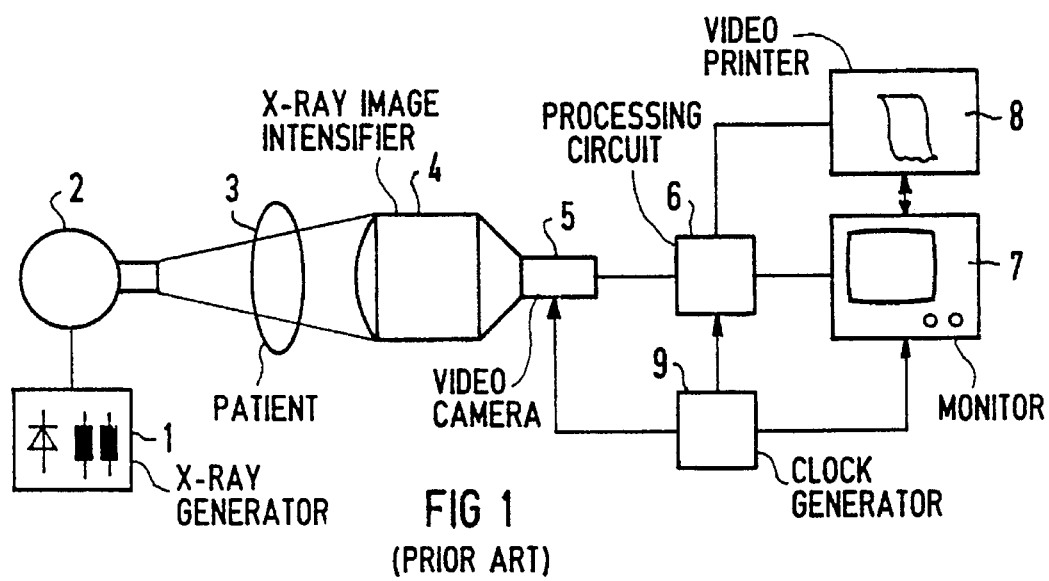
FIG. 1 is a known x-ray diagnostics installation of the prior art comprising a video printer.

FIG. 1 shows a known x-ray diagnostics installation of the prior art comprising an x-ray generator 1 that is connected to an x-ray tube 2 that generates a ray beam that penetrates a patient 3. The x-ray beam attenuated according to the transparency of the patient 3 is incident onto the input luminescent screen of an x-ray image intensifier 4 that is coupled to a video camera 5 for conversion of the x-ray image into an electrical signal sequence. A processing circuit 6 can be connected to the video camera 5, this processing circuit 6 being connected to a monitor 7 for visual reproduction and to a video printer 8 for producing a hard copy. A clock generator 9 thereby generates the control and synchronization signals for the video chain 5 through 8. The processing circuit 6 can, for example, thereby comprise amplifiers, calculating means or image stores.

Figure 2:
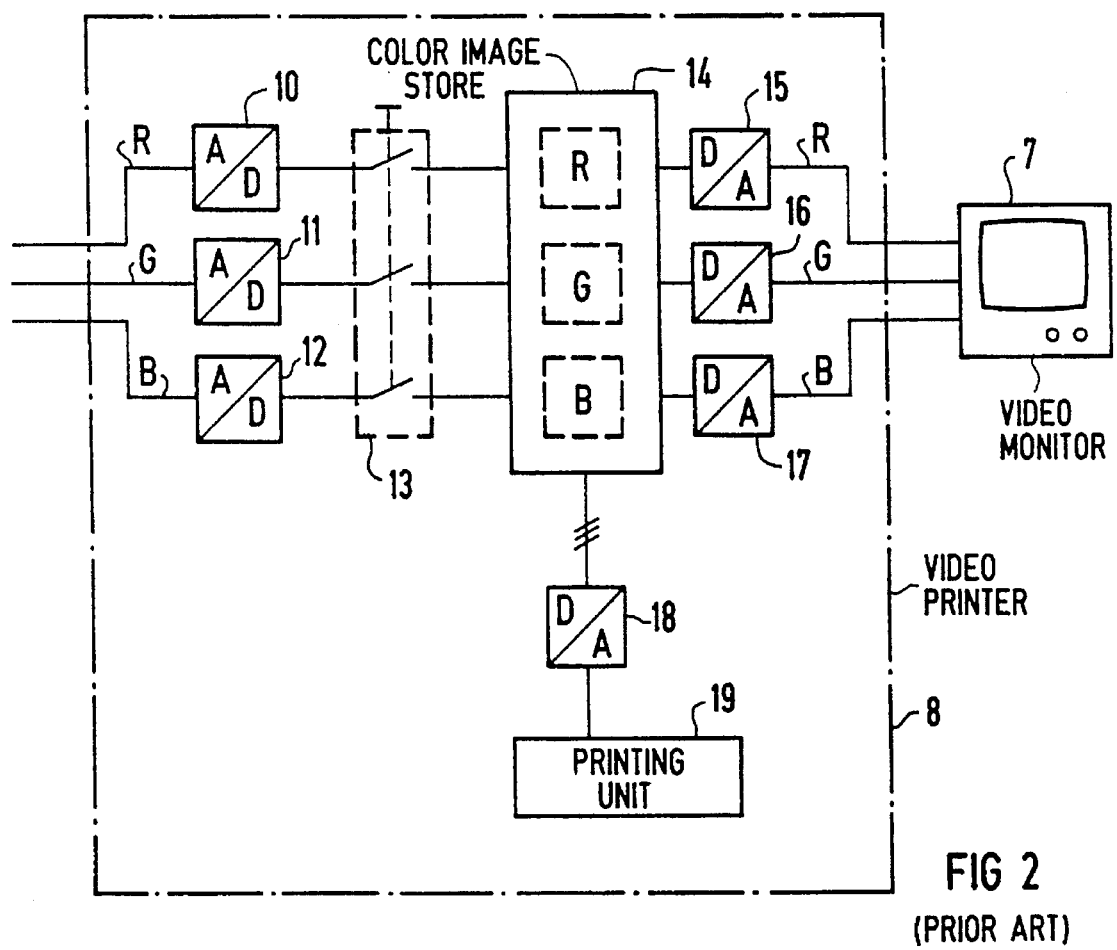
FIG. 2 is a known video printer of the x-ray diagnostics installation of FIG. 1.

The video printer 8 of the prior art shown in FIG. 1 has already been discussed in greater detail with reference to FIG. 2.

According to the invention, this video printer 8 can have the structure shown in FIG. 3. The video printer 8 can be supplied with the black-and-white signal B/W via a video amplifier 21 that is connected to three video distributing or isolating amplifiers 22 through 24. The outputs of the video distributing amplifiers 22 through 24 are connected to the three A/D converters 10 through 12 via a switch unit 20 whose function shall be set forth later. The digital outputs of the A/D converters 10 through 12 are connected to the color image store 14 or the video printer 8 via three switch units 25 through 27. The outputs of the color image store 14 are in communication with the monitor 7 in a known way via D/A converters 15 through 17, whereas they are connected to the printing unit 19 of the video printer 8 via a further D/A converter 18. A control unit 28—as a clock generator—effects the control of the switch units 20 and 25 through 27.

When chronological progressions are then to be produced from the video signal of a video camera 5 (the black-and-white signal B/W), then all switch units 25 through 27 are switched on at the beginning of the exposures, so that the video signal is read into all three image stores 14R, 14B, and 14G of the color image store 14. At time t1 that can correspond to the maximum arterial phase given a DSA exposure, the first switch unit 25 is opened, so that the roll-in of the video signal into the image store of the red color channel R of the color image store 14 is stopped. At a second time t2, which can correspond to the maximum intermediate phase (arterial/venous), the second switch unit 26 is opened, so that the roll-in into the image store of the green color channel G of the color image store 14 is interrupted. Controlled by the control unit 28, the third switch unit 27 is opened at time t3 which can correspond to the point in time of the maximum venous phase, so that the roll-in into the image store of the last, blue color chanel B of the color image store 14 is now interrupted. The image now contained in the color image store 14 and having different chronological information can be monitored via the monitor 7 and can be printed out on the printing unit 19 of the video printer 8. The chronological path of the contrast agent may be seen on the basis of the different colors.

The switch unit 20 that effects a switching of the three color channels R, G, and B of the video printer 8 from the video distributing amplifiers 22 through 24 onto the RGB inputs of the video printer 8 is provided so that the video printer 8 can also process the standard signals of the color channels R, G, and B. When a switch to this mode is undertaken, then the switch units 25 through 27 are closed, influenced by the control unit 28, so that a direct connection of the RGB inputs to the color image store 14 is established.

As shown, this circuit can be contained in the video printer 8 and can form a unit with it. However, it can also precede the RGB inputs and be arranged in the processing circuit 6.

As a result of this successive image input, one obtains an x-ray diagnostics installation with video printer 8 which enables a simple, easily operated color presentation of chronological differences, particularly differences in the contrast agent during the venous and arterial phase in a color image, or spatial differences given a stereo technique. Despite an input that occurred chronologically successively, the resulting color image can be monitored before being printed out as a result of the roll-in in the color image store and the connection thereof to the color monitor 7.

Although various minor changes and modifications might be suggested by those skilled in the art, it will be understood that I wish to include within the claims of the patent warranted hereon all such changes and modifications as reasonably come within my contribution to the art.

I claim as my invention:

1. A circuit arrangement for reproduction of an RGB (red, green, blue) color image of a color video signal or of single color R, G, or B chronologically presented color images from a B/W (black and white) video signal, comprising:

first inputs for color channels R, G, B (red, green, blue) for the color video signal;

a second input for receiving the B/W (black and white) video signal;

a reproduction unit having individual color channels R, G, B;

a first switch unit for alternatively connecting either said first inputs for the color video signal through to said R, G, B color channels of the reproduction unit or for switching through said second input for the B/W video signal to the R, G, B color channels of the reproduction unit; and a second switch unit connected between the reproduction unit and the first switch unit for producing three chronologically presented images when the first switch unit is switching through the second input so that the B/W video signals are applied to the individual color channels R, G, B of the reproduction unit at different times thus producing the different single color R, G, or B images, or when said first switch unit is switching through the first inputs for the color channels R, G, B, then said second switch unit providing a connection for all of the R, G, B color channels to the R, G, B color channels of the reproduction unit for reproduction of said RGB color image.

2. The circuit arrangement according to claim 1 wherein the second switch unit comprises three separate switches connected to a control unit for individually operating the three switches at different times.

3. The circuit arrangement according to claim 1 wherein the first switch unit comprises a separate switch connecting to each of the R, G, B channel inputs.

4. A circuit arrangement according to claim 1 wherein an image store is provided for every color channel.

5. A circuit arrangement according to claim 1 wherein the reproduction unit comprises a video printer.

6. A circuit arrangement for reproduction of an RGB (red, green, blue) color image of a color video signal or of single color R, G, or B chronologically presented color images from a B/W (black and white) video signal, comprising:

first inputs for color channels R, G, B (red, green, blue) for the color video signal;

a second input for receiving the B/W (black and white) video signal;

a reproduction unit having individual color channels R, G, B;

a first switch unit for alternatively connecting either said first inputs for the color video signal through to said R, G, B color channels of the reproduction unit or for switching through said second input for the B/W video signal to the R, G, B color channels of the reproduction unit; and a second switch unit connected between the reproduction unit and the first switch unit for producing three chronologically presented images when the first switch unit is switching through the second input so that the B/W video signals are applied to the individual color channels R, G, B of the reproduction unit at different times thus producing the different single color R, G, or B images, or when said first switch unit is switching through the first inputs for the color channels R, G, B, then said second switch unit providing a connection for all of the R, G, B color channels to the R, G, B color channels of the reproduction unit for reproduction of said RGB color image; and the second switch unit providing the single color R, G, or B chronologically presented color images such that video signals relating to digital subtraction angiography are switched through by a first of three switches of the second switch unit at a point in time of maximum arterial phase.

7. A circuit arrangement for reproduction of an RGB (red, green, blue) color image of a color video signal or of single color R, G, or B chronologically presented color images from a B/W (black and white) video signal, comprising:

first inputs for color channels R, G, B (red, green, blue) for the color video signal;

a second input for receiving the B/W (black and white) video signal;

a reproduction unit having individual color channels R, G, B;

a first switch unit for alternatively connecting either said first inputs for the color video signal through to said R, G, B color channels of the reproduction unit or for switching through said second input for the B/W video signal to the R, G, B color channels of the reproduction unit; and a second switch unit connected between the reproduction unit and the first switch unit for producing three chronologically presented images when the first switch unit is switching through the second input so that the B/W video signals are applied to the individual color channels R, G, B of the reproduction unit at different times thus producing the different single color R, G, or B images, or when said first switch unit is switching through the first inputs for the color channels R, G, B, then said second switch unit providing a connection for all of the R, G, B color channels to the R, G, B color channels of the reproduction unit for reproduction of said RGB color image; and the second switch unit providing the single color R, G, or B chronologically presented color images such that video signals relating to digital subtraction angiography are switched through by a first of three switches of the second switch unit at a point in time of maximum arterial phase.

8. A circuit arrangement for reproduction of a three color image of a color video signal or of single first, second, or third color chronologically presented color images from a B/W (black and white) video signal, comprising:

first inputs for first, second, and third color channels for the color video signal;

a second input for receiving the B/W (black and white) video signal;

a reproduction unit having individual first, second, and third color channels;

a first switch unit for alternatively connecting either said first inputs for the color video signal through to said first, second, and third color channels of the reproduction unit or for switching through said second input for the B/W video signal to the first, second, and third color channels of the reproduction unit; and a second switch unit connected between the reproduction unit and the first switch unit for producing three chronologically presented images when the first switch unit is switching through the second input so that the B/W video signals are applied to the individual first, second, and third color channels of the reproduction unit at different times thus producing the different single first, second, or third color images, or when said first switch unit is switching through the first inputs for the first, second, and third color channels, then said second switch unit providing a connection for all of the first, second, and third color channels to the first, second, and third color channels of the reproduction unit for reproduction of said three color image.

9. A circuit arrangement for reproduction of an RGB (red, green, blue) color image of a color video signal or of single color R, G, or B chronologically presented color images from a B/W (black and white) video signal, comprising:

first inputs for color channels R, G, B (red, green, blue) for the color video signal;

a second input for receiving the B/W (black and white) video signal;

a reproduction unit having individual color channels R, G, B;

a first switch unit for alternatively connecting either said first inputs for the color video signal through to said R, G, B color channels of the reproduction unit or for switching through said second input for the B/W video signal to the R, G, B color channels of the reproduction unit; and a second switch unit connected between the reproduction unit and the first switch unit for producing three chronologically presented images when the first switch unit is switching through the second input so that the B/W video signals are applied to the individual color channels R, G, B of the reproduction unit at different times thus producing the different single color R, G, or B images, or when said first switch unit is switching through the first inputs for the color channels R, G, B, then said second switch unit providing a connection for all of the R, G, B color channels to the R, G, B color channels of the reproduction unit for reproduction of said RGB color image; and the second switch unit providing the single color R, G, or B chronologically presented color images such that video signals relating to digital subtraction angiography are switched through by a first of three switches of the second switch unit at a point in time of maximum arterial phase.

* * * * *